United States Patent [19]

Duffett

[11] Patent Number: Plant 6,905

[45] Date of Patent: Jul. 4, 1989

[54] CHRYSANTHEMUM PLANT NAMED MESMER

[75] Inventor: William E. Duffett, Salinas, Calif.

[73] Assignee: Yoder Brothers, Inc., Ashtabula, Ohio

[21] Appl. No.: 190,692

[22] Filed: May 5, 1988

[51] Int. Cl.[4] ..... A01H 5/00

[52] U.S. Cl. ..... Plt./79

[58] Field of Search ..... Plt./79

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Mesmer particularly characterized by its flat capitulum form; decorative capitulum type; orange-bronze ray floret color; diameter across face of capitulum of up to 75 mm at maturity; uniform nine week photoperiodic flowering response to short days; peduncle length ranging from 6 to 15 cm on open, terminal sprays; and medium plant height when grown as a single stem spray cut mum.

3 Drawing Sheets

The present invention comprises a new and distinct cultivar of Chrysanthemum, botanically known as *Dendranthema grandiflora,* and referred to by the cultivar name Mesmer.

Mesmer, identified as 81075001, was originated from a cross made by William E. Duffett in a controlled breeding program in Salinas, Calif. in 1980.

The female parent and the male parent of Mesmer were both unnamed seedlings, identified respectively as 70098002 and 78943006.

Mesmer was discovered and selected as one flowering plant within the progeny of the stated cross by William E. Duffett in August 1981 in a controlled environment in Salinas, Calif.

The first act of asexual reproduction of Mesmer was accomplished when vegetative cuttings were taken from the initial selection in October 1981 in a controlled environment in Salinas, Calif., by technicians working under formulations established and supervised by William E. Duffett.

Horticultural examination of controlled flowerings of successive plantings has shown that the unique combination of characteristics as herein disclosed for Mesmer are firmly fixed and are retained through successive generations of asexual reproduction.

Mesmer has not been observed under all possible environmental conditions. The phenotype may vary significantly with variations in environment such as temperature, light intensity, and daylength.

The following observations, measurements and comparisons describe plants grown in Salinas, Calif. under greenhouse conditions which approximate those generally used in commercial greenhouse practice.

The following traits have been repeatedly observed and are determined to be basic characteristics of Mesmer, which, in combination, distinguish this Chrysanthemum as a new and distinct cultivar:

1. Flat capitulum form.
2. Decorative capitulum type.
3. Orange-bronze ray floret color.
4. Diameter across face of capitulum up to 75 mm at maturity.
5. Uniform nine week photoperiodic flowering response to short days.

6. Peduncle length ranging from 6 to 15 cm on open terminal sprays.
7. Medium plant height, requiring 1 to 2 long day weeks prior to short days to attain a flowered plant height of 90 to 100 cm for year-round flowerings.

The accompanying photographic drawings show typical inflorescence and leaf characteristics of Mesmer, with the colors being as nearly true as possible with illustrations of this type.

Sheet 1 is a color photograph of Mesmer grown as a single stem cut spray mum.

Sheet 2 is a black and white photograph of three views of the inflorescence of Mesmer.

Sheet 3 is a black and white photograph showing the upper and under sides of the leaves of Mesmer at three stages of development (mature, intermediate and immature).

Of the commercial cultivars known to the inventor, the most similar in comparison to Mesmer is Falma, disclosed in the inventor's U.S. Plant Pat. No. 5,996. Reference is made to Chart A, which compares certain characteristics of Mesmer to the same characteristics of Falma. Similar traits are ray floret color, capitulum form and type, and flowering response. The peduncle length of Mesmer is shorter, and the diameter of capitulum is larger than Falma. With the same number of long days prior to start of short days, Mesmer has a shorter plant height than Falma.

In the following description, color references are made to The Royal Horticultural Society Colour Chart. The exact color for corolla of ray florets of Mesmer is not represented in the R.H.S. Colour Chart, and the color values given are those closest to the actual color of Mesmer. The color values were determined on plant material grown in Salinas, Calif. on Oct. 8, 1987.

Classification:

*Botanical.*—*Dendranthema grandiflora,* cv Mesmer.

*Commercial.*—Decorative cut spray mum.

INFLORESCENCE

A. Capitulum:

*Form.*—Flat.

*Type.*—Decorative.

*Diameter across face.*—Up to 75 mm at maturity.

B. Corolla of ray florets:

*Color (general tonality from a distance of three meters).*—Orange-bronze.

*Color (upper surface).*—163A to 163B, overlaid with 167A to 167B.

*Color (under surface).*—12A overlaid with 169D.

*Shape.*—Longitudinal axis, straight. Cross section of ray, straight. Tip of ray, rounded.

C. Corolla of disc florets:

*Color (mature).*—Closest to 5A.

*Color (immature).*—Closest to 151B to 151C. Very few disc florets, which are not visible in mature flower.

D. Reproductive organs:

*Androecium.*—Present on disc florets only, very few; very scant pollen.

*Gynoecium.*—Present on both ray and disc florets.

PLANT

A. General appearance:

*Height.*—Medium; 90 to 100 cm as a single stem cut mum with 1 to 2 long day weeks prior to short days.

B. Foliage:

*Color (upper surface).*—147A.

*Color (under surface).*—147B.

*Shape.*—Deeply lobed and serrated.

CHART A

COMPARISON OF MESMER AND FALMA

| | Mesmer | Falma |
|---|---|---|
| Ray floret color | Orange Bronze | Yellow Orange |
| Capitulum form and type | Flat Decorative | Flat Decorative |
| Spray formation | Terminal 6 to 15 cm peduncles | Terminal 15 to 25 cm peduncles |
| Diameter across face of capitulum | Up to 75 mm | Up to 6.5 cm |
| Plant height | Medium | Tall |
| Flowering response period | 9 weeks | 9 weeks |

COMPARISONS MADE OF PLANTS GROWN AS SINGLE STEM SPRAY CUT MUMS IN SALINAS, CALIFORNIA

I claim:

1. A new and distinct Chrysanthemum plant named Mesmer, as described and illustrated, and parts thereof.

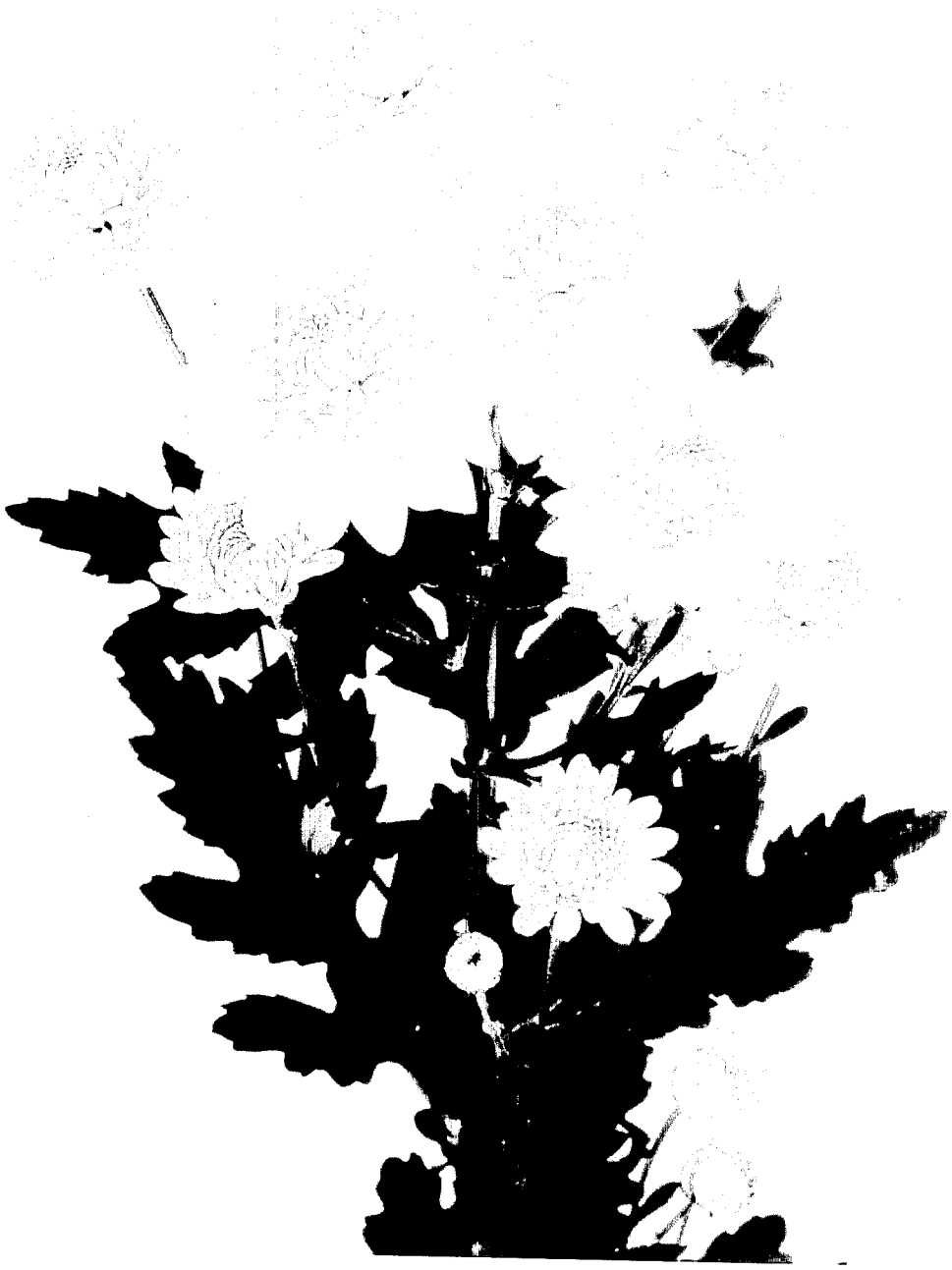

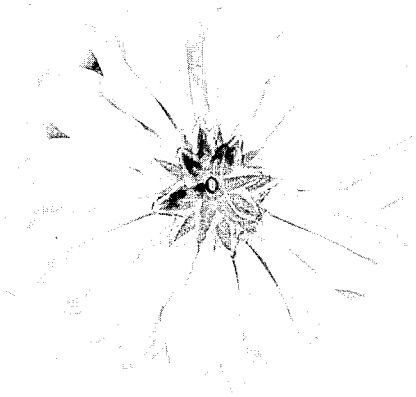
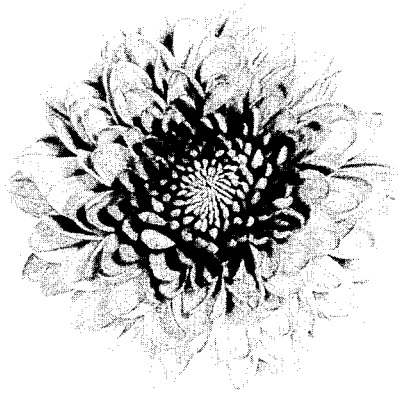
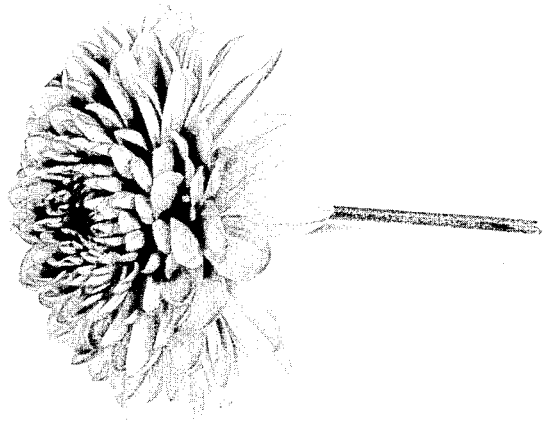

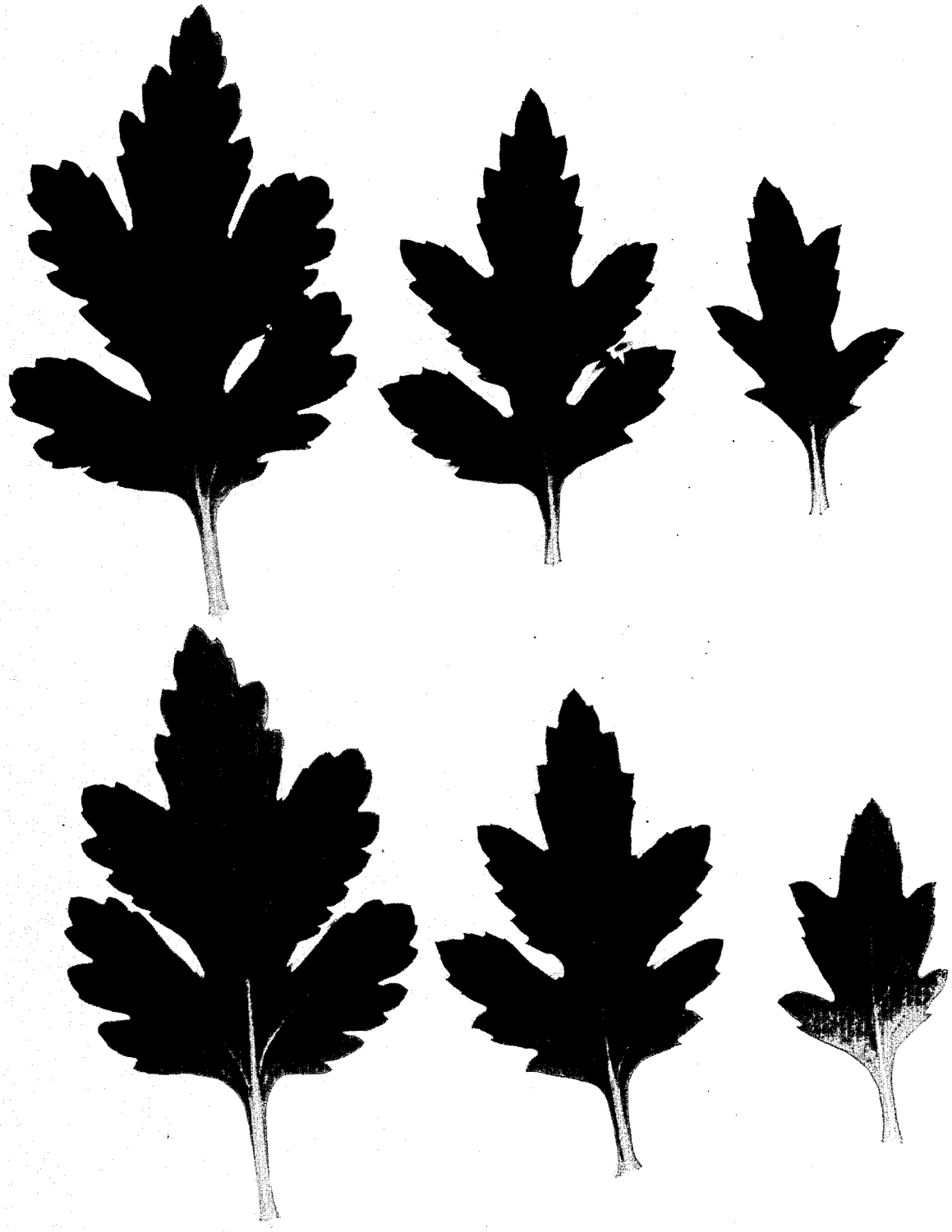

* * * * *